United States Patent [19]

Herzog et al.

[11] Patent Number: 5,407,888
[45] Date of Patent: Apr. 18, 1995

[54] SILVER CATALYST

[75] Inventors: Klaus Herzog; Stefan Boeck, both of Ludwigshafen; Wolf D. Mross, Frankenthal; Juergen Plueckhan; Karl-Heinz Boehning, both of Frankenthal; Ewald Gallei, Viernheim, all of Germany

[73] Assignee: BASF Aktiengesellschaft, Ludwigshafen, Germany

[21] Appl. No.: 59,538

[22] Filed: May 10, 1993

[30] Foreign Application Priority Data

May 12, 1992 [DE] Germany ............... 42 15 493.6

[51] Int. Cl.$^6$ .......................................... B01J 23/50
[52] U.S. Cl. .................................... 502/317; 502/344; 502/348
[58] Field of Search ................. 502/371, 344, 348

[56] References Cited

U.S. PATENT DOCUMENTS

| | | |
|---|---|---|
| 2,294,383 | 9/1942 | Carter . |
| 3,172,893 | 3/1965 | Ameen . |
| 3,423,328 | 1/1969 | Keith et al. . |
| 3,962,136 | 6/1976 | Nielson et al. . |
| 4,007,135 | 2/1977 | Hayden et al. . |
| 4,732,918 | 3/1988 | Lohmueller et al. . |
| 4,740,493 | 4/1988 | Boehning et al. . |
| 4,820,675 | 4/1989 | Lauritzen ............... 502/348 |
| 4,908,343 | 3/1990 | Bhasin ................... 502/317 |
| 5,057,481 | 10/1991 | Bhasin ................... 502/347 |

FOREIGN PATENT DOCUMENTS

| | | |
|---|---|---|
| 82609 | 11/1983 | European Pat. Off. . |
| 266015 | 10/1987 | European Pat. Off. . |
| 357293 | 8/1990 | European Pat. Off. . |
| 105750 | of 1981 | Japan . |
| 1413251 | 11/1975 | United Kingdom . |
| 1512625 | 6/1978 | United Kingdom . |

OTHER PUBLICATIONS

Brunauer et al., J. Am. Chem. Soc., vol. 60, pp. 309–319 (1938).

Ullmann's Encyclopedia of Industrial Chemistry, 5th Ed., vol. 10A, pp. 117–135 (1987).

Primary Examiner—Anthony McFarlane
Attorney, Agent, or Firm—John H. Shurtleff

[57] ABSTRACT

A silver catalyst containing one or more alkali metals and also tungsten as promotors for the direct oxidation of ethylene with oxygen to form ethylene oxide, on a porous support substantially consisting of α-aluminum oxide and having a specific surface area (BET) of from 0.3 to 3 m$^2$/g, which contains tungsten in a concentration of from 60 to 330 ppmwt, based on the total catalyst, per m$^2$ of surface area for each gram of supporting material.

8 Claims, No Drawings

SILVER CATALYST

The present invention relates to a silver catalyst containing one or more alkali metals and also tungsten as promotors for the direct oxidation of ethylene with oxygen to form ethylene oxide, on a porous support substantially consisting of α-aluminum oxide and having a specific surface area (BET) of from 0.3 to 3 mm$^2$/g.

To prepare ethylene oxide by the direct oxidation of ethylene with oxygen use is made of silver-containing catalysts. In these catalysts usually α-aluminum oxide serves as support for the catalytically active silver phase. In addition additives can be included in small quantities to promote the catalytic properties of the catalyst.

The silver and any dopants to be added to the catalyst can be applied to the support by various methods (cf U.S. Pat. No. 2,294,383, U.S. Pat. No. 3,423,328, U.S. Pat. No. 3,172,893). Usually an impregnating process is used, in which the supporting material is impregnated with a solution of a suitable precursor stage, e.g., a (silver salt)/amine complex or a silver carboxylate. Following the impregnation with a solution of the silver compound or with a solution which contains the silver compound and the promotor compounds, the catalyst precursors thus produced are usually heated to temperatures at which the silver compound dissociates to give metallic silver.

As mentioned above, there can be added to the silver catalysts, to improve their efficiency and in particular their selectivity, promotors selected from the alkali metals, more preferably the alkali metals lithium, cesium, and rubidium (cf, e.g., DE-A 2,300,512, DE-A 2,753,359, EP-A 211,397).

JP-A 105,750 (1981) discloses silver catalysts which may be doped with tungsten in addition to alkali metal promotors, preferably cesium. These catalysts contain, besides silver, from 0.01 to 0.05 gram equivalents per kg of catalyst of a complex compound of tungsten with an alkali metal, in which the atomic ratio of alkali metal to tungsten is between 2:1 and 1:2, over a surface area of from 1 to 5m$^2$/g of supporting material. Cesium tungstate (Cs$_2$WO$_4$) is preferably used. Accordingly, these catalysts have a cesium content ranging from 2660 to 13000 ppmwt and a tungsten content ranging from 1840 to 13300 ppmwt, based, in each case, on the total catalyst, equivalent to an amount of at least roughly 370 ppmwt of tungsten, based on the total catalyst, per m$^2$ of the specific surface area (BET) for each gram of supporting material. According to said reference, the cesium and tungsten contents of the catalysts revealed therein increase with increasing surface area of the substrate used. Consequently, the least possible tungsten content of these catalysts of 370 ppmwt, based on the total catalyst, per m$^2$ of surface area per gram of substrate, as determined purely arithmetically, is to be regarded as being unfavorable according to the teaching of said reference.

EP-A 266,015 discloses that a considerable improvement in selectivity can be achieved by the addition of small amounts of rhenium to the silver catalyst, which improvement declines relatively steeply, however, when such catalysts are used in large scale ethylene oxide syntheses, so that these catalysts have only a short working period. According to the examples of this reference, in addition to rhenium tungsten can be included as dopant in these silver catalysts.

According to DE-A 2,454,972, the addition of a number of elements, in particular barium, chromium, calcium, magnesium, and strontium and also copper, gold, zinc, cadmium, mercury, niobium, tantalum, molybdenum, tungsten and vanadium, improves the properties of silver catalysts used for the preparation of ethylene oxide and having a silver content between 3 and 15 wt %. This reference states a wide range of tungsten contents—from 0.052 to 2570 ppmwt, based on the final catalyst—for said amounts of silver and for specific surface areas (BET) of the substrate of from 0.04 to 10 m$^2$/g. However, this reference does not specify the nature of the said improvement in the properties of the silver catalysts, and neither does it document it in examples. Industrial uses of tungsten-doped silver catalysts are not as yet known in the art.

According to EP-A 357,293, silver catalysts can be used for the preparation of ethylene oxide, and these can be doped inter alia with tungsten in addition to alkali metals and must obligatorily contain sulfur. A disadvantage of these catalysts is their low activity, expressed in terms of the operating temperature necessary for a 30% oxygen conversion, which in the case of these catalysts is usually well above 230° C. Because of the high operating temperatures required to achieve satisfactory conversion these catalysts age faster than those which show good activity at lower temperatures, with the result that the activity drops relatively rapidly and to such an extent that it is necessary to use reaction temperatures at which water-cooled reactors can be no longer operated without having been subjected to additional uneconomical structural modifications.

As far as we know, tungsten-doped silver catalysts have not yet been used in industrial processes for the preparation of ethylene oxide. The reason for this is that doping with tungsten reduces the activity of the silver catalysts to such an extent that the high temperatures required for long-term usage of these catalysts cannot be attained in pressure-water-cooled tube bundle reactors normally used for the preparation of ethylene oxide on an industrial scale, unless extensive structural modifications are carried out on these reactors.

Ethylene oxide is a basic chemical which is produced in large quantities worldwide. There is therefore a need for further improved catalysts for the manufacture of this compound. It is an object of the present invention to provide silver catalysts for ethylene oxide synthesis which show improved selectivity and at the same time exhibit high activity.

Accordingly, we have found a silver catalyst containing one or more alkali metals and also tungsten as promotors for the direct oxidation of ethylene with oxygen to form ethylene oxide, on a porous support substantially consisting of α-aluminum oxide and having a specific surface area (BET) of from 0.3 to 3 m$^2$/g, which contains tungsten in a concentration of from 60 to 330 ppmwt, based on the total catalyst, per m$^2$ of surface area for each gram of supporting material.

We have found that there is a very narrow optimum range for the tungsten content of the catalysts and that the low amount of tungsten required bears a direct relationship to the surface area of the support. A catalyst which is particularly advantageous with regard to selectivity and activity for the direct oxidation of ethylene with oxygen to form ethylene oxide is obtained by applying between 10 and 30 wt % of silver to a support composed of α-aluminum oxide of high purity and having a specific surface area (BET) of from 0.3 to 3.0 m²/g, in particular of from 0.5 to 2.0 m²/g, and additionally incorporating into the catalyst from 100 to 1000 ppmwt and preferably from 150 to 800 ppmwt and more preferably from 200 to 500 ppmwt of lithium and/or from 200 to 2000 ppmwt, preferably from 300 to 1600 ppmwt and more preferably from 450 to 1300 ppmwt of cesium, based, in each case, on the final catalyst, and also from 60 to 330 ppmwt and preferably from 75 to 280 ppmwt and more preferably from 95 to 230ppmwt and most preferably from 105 to 160 ppmwt of tungsten, based on the total catalyst, per m² of specific surface area (BET) for each gram of supporting material. *J. Am. Chem. Soc.* 60, 309 (1938) describes the BET method of determining the specific surface area. The anions of the deposited components have no significant influence on the action of the catalyst and, for example, oxides, nitrates, halides, phosphates, carbonates, and carboxylates can be used. It is also possible to precipitate the alkali metals completely or advantageously partially in the form of salts of complex oxygen compounds of tungsten, for example, in the form of the respective alkali metal tungstates, on to the catalyst support.

When preparing the silver catalysts, the cesium can be partially or entirely replaced by rubidium. In this case, advantageously from 150 to 2000 ppmwt, preferably from 200 to 1100 ppmwt and more preferably from 300 to 900 ppmwt of rubidium are applied, based on the final catalyst. Likewise, the lithium can be partially or completely replaced by rubidium and/or cesium in the tungsten-doped silver catalyst. Combinations with other alkali metal promoters, such as sodium and/or potassium, are also possible.

The silver catalyst of the invention for the preparation of ethylene oxide has the advantage that the selectivity improvement must not be aquired at the expense of a drastic impairment of the activity of the catalyst, which would render the catalyst useless for many industrial plants. Surprisingly, the addition of tungsten in the catalyst of the invention effects no or only slight reduction in activity whilst at the same time it raises the selectivity, as compared with prior art silver catalysts.

The catalysts of the invention consist of the catalytically active components silver, tungsten, and advantageously one or more of said alkali metals, applied to a supporting material. Various types of porous material can be used as supporting material, such as activated charcoal, titanium dioxide, or silicon dioxides, or ceramic compositions, such as are also mentioned in the aforementioned literature.

Particularly advantageously for the silver catalysts of the invention is the use of an α-aluminum oxide support which consists of α-aluminum oxide of high purity, having an α-aluminum oxide content of more than 99 wt % and preferably of more than 99.5 wt %. Characteristic data of suitable α-aluminum oxide supports are listed in Table 1 below.

The geometric form of the support, particles is of less importance with respect to the catalytic properties, provided the particles are sufficiently small to make it possible for the gases involved in the reaction to diffuse to the total catalytically effective surface under the reaction conditions and the geometric form does not otherwise impair the process parameters, in particular the dissipation of heat produced by the reaction. For example, the support particles may be in the form of balls, cylinders, elliptic molded articles, spirals or, preferably, rings.

The catalytically effective metal components are advantageously applied to the support, by an impregnation technique. The metal components can be applied to the substrate in one or more impregnation steps. The impregnating solution can, particularly in the case of a single-stage impregnation process, contain the salts of all of the catalytically active components. Alternatively, the silver can be applied to the support first, to be followed by the alkali metals and the tungsten, or another alternative is to deposit the silver and part of the alkali metals, for example the lithium, on to the support in a separate step and then to dope the substrate with the remaining alkali metal and the tungsten. After each of these impregnation steps, the supports thus treated can be dried and calcined in one or more stages to cause the silver salt used for the impregnation to be decomposed to produce metallic silver. To this end, the catalyst is generally heated to temperatures of from 180° to 300° C. until the silver compound used has decomposed to form elementary silver.

The silver is usually applied to the support in the form of silver salt solutions and preferably in the form of silver salt solutions which are stabilized with ammonia or with amines, as described in DE-A 2,521,906 or DE-A 2,300,512. The tungsten can be applied to the support together with these impregnating solutions, e.g., in the form of tungsten oxide, ortho-tungstic acid, isopolytungstic acid, para-tungstic acid, or meta-tungstic acid and/or in the form of their alkali metal salts and/or ammonium salts.

The anions of the metal salts in the impregnating solutions can be chosen virtually arbitrarily. For example, the impregnating solution can contain the metals to be applied in the form of their hydroxides, nitrates, halides, phosphates, carbonates, or carboxylates; nitrates and carboxylates being preferred. Of the carboxylates, the oxalates are particularly preferred.

Using the catalysts of the invention, ethylene oxide can be produced by conventional methods by the direct oxidation of ethylene with oxygen. To achieve this end, it is possible to use all reactors which can be employed in prior art processes for the manufacture of ethylene oxide, for example, the externally cooled tube bundle reactors normally used in industrial plants (cf *Ullmann's Ecyclopedia of Industrial Chemistry*; 5th Edition; Vol. 10; pp. 117 to 135, 123 to 125; VCH Verlagsgesellschaft, Weinheim 1987) and also reactors having a loose bed of catalyst and cooling tubes, for example, the reactors described in DE-A 3,414,717, EP-A 82,609 and EP-A 339,748. Particularly preferred for the preparation of ethylene oxide are catalysts of the invention used in combined layers of catalyst, as described in German Patent Application No. P 42 05 090.1.

To prepare ethylene oxide from ethylene and oxygen using the catalysts of the invention operations can be carried out under conventional reaction conditions. To the ethylene and molecular oxygen-containing reaction gas there can be additionally added inert gases, such as nitrogen or gases which are inert under the conditions used for the reaction, such as steam or methane, and also, if desired, moderators (inhibitors), for example halogenated hydrocarbons such as vinyl chloride or 1,2-dichloroethane, can be admixed therewith. Advantageously the oxygen content of the reaction gas is in a range in which no explosive gas mixtures occur. A suitable composition of the reaction gas for the preparation of ethylene oxide can comprise, e.g., ca 30 vol % of ethylene, ca 8 vol % of oxygen and from ca 0.5 to 5 ppm of a chlorine-containing inhibitor, such as vinyl chloride or dichloroethane, whilst the remainder of the reaction gas can usually be composed of hydrocarbons such as methane or ethane, or alternatively inert gases such as nitrogen. In addition, other substances can be included in the reaction gas, such as steam, carbon dioxide or noble gases. Oxidation carried out using the catalysts of the invention is effected at temperatures of from 180° to 300° C. and preferably from 200° to 250° C.

Advantageously, the preparation of ethylene oxide from ethylene and oxygen can be carried out in a recycle process. The reaction gas mixture is circulated through the reactor and following each pass the newly formed ethylene oxide and the byproducts formed during the reaction are removed from the stream of gaseous products, which is recycled to the reactor following replenishment with the requisite amounts of ethylene, oxygen, and reaction moderators. The separation of the ethylene oxide from the stream of gaseous products and purification thereof can be carried out by conventional prior art methods (cf *Ullmann's Encyclopedia of Industrial Chemistry* 5th Edition; Vol. 10; pp. 117 to 135, 123 to 125; VCH Verlagsgesellschaft, Weinheim 1987).

EXAMPLES

The supporting materials used for the catalysts to be prepared were α-aluminum oxides having a purity greater than 99% in the form of rings having the dimensions 8·8·2 mm (diameter·height·wall thickness). Important characteristic data of the supports used in the following examples and bearing the designations I, II, and III are listed in Table 1 below.

TABLE 1

Characteristic Data of the Supporting Materials Used

| Supports | I | II | III |
|---|---|---|---|
| Content of SiO$_2$ (wt %) | 0.2 | 0.5 | 0.25 |
| Soluble Ions (ppmwt) | | | |
| Al | 300 | 570 | 350 |
| Ca | 500 | 340 | 280 |
| K | 15 | 140 | 75 |
| Na | 50 | 150 | 110 |
| Specific Surface Area (BET) (m$^2$/g) | 0.3 | 0.9 | 1.8 |
| Cold Water Intake (20° C., mL/g) | 0.22 | 0.45 | 0.53 |
| Porosity (%) | 50 | 67 | 70 |
| Average Pore-Diameter (μm) | | | |
| First distribution | 2.0 | 3.1 | 18.0 |
| Second distribution | — | — | 0.5 |
| Abrasion (wt %) | 5 | 2.1 | 1.3 |

The determination of the content of soluble ions was carried out as follows: ca 10 g of support particle were weighed accurately and then boiled with semiconcentrated nitric acid for a period of 10 min. The filtered solution of the resulting extract was used for quantitative determination of the said elements by means of atom-absorption spectrometry.

The SiO$_2$ content of the support was determined by photometric techniques by measuring, at a wavelength of 820 min, the absorbance of the blue silicon/molybdate complex which forms on alkaline solubilization of a sample of the substrate and reaction of the resulting solution with ammonium heptamolybdate.

COMPARATIVE CATALYST 1

The comparative catalyst 1 was a commercial silver catalyst doped with cesium. The results obtained by the test method described below and carried out on this catalyst are listed in Table 3 below.

COMPARATIVE CATALYST 2

A solution containing 14.3 parts by weight of silver nitrate, 0.136 parts by weight of lithium nitrate, 12.6 parts by weight of sec-butylamine, and 2.1 parts by weight of water, was admixed with a second solution comprising 0.0185 parts by weight of cesium hydroxide and 0.0594 parts by weight of ortho-tungstic acid (H$_2$WO$_4$) in 1 part by weight of 10 wt % strength ammonia solution in water. 100 parts by weight of the α-aluminum oxide support I were impregnated with this solution and then convened to the final catalyst in a belt-type calciner, at a temperature of 220° C., over a period of 10 min. Comparative catalyst 2 is equivalent to a catalyst as described in DE-A 12,454,972. The results obtained by the test method carried out on this catalyst are listed in Table 3 below.

Catalyst A

Following the method used in Example 2, a catalyst was prepared using the following amounts of starting materials:

100 parts by weight of α-aluminum oxide II, 29.3 parts by weight of silver nitrate, 0.295 parts by weight of lithium nitrate, 25.9 parts by weight of sec-butylamine, 5.3 parts by weight of water, 0.0737 parts by weight of cesium hydroxide, 0.0194 parts by weight of ortho-tungstic acid (H$_2$WO$_4$), 1 part by weight of a 10 wt % strength ammonia solution in water. The test method results achieved using catalyst A in the preparation of ethylene oxide are listed in Table 3 below.

Catalyst B

Following the method used in Example 2, catalyst B was prepared using the following amounts of starting materials:

100 parts by weight of α-aluminum oxide III, 34.6 parts by weight of silver nitrate, 0.3 parts by weight of lithium nitrate, 6.4 parts by weight of water, 30.5 parts by weight of sec-butylamine, 0.1032 parts by weight of cesium hydroxide, 0.0932 parts by weight of ortho-tungstic acid (H$_2$WO$_4$) and 1 part by weight of a 10 wt % strength aqueous ammonia solution. The test results obtained using catalyst B in the preparation of ethylene oxide from ethylene and oxygen according to the test method described below are listed in Table 3 below.

The metal contents of comparative catalyst 2 and of catalysts A and B of the invention are given in Table 2 below.

TABLE 2

Metal Contents of Catalysts A, B and Comparative Catalyst 2

| Catalyst | Comparative Catalyst 2 | A | B |
|---|---|---|---|
| silver [wt %] | 8.3 | 15.7 | 18.0 |
| lithium [ppmwt] | 125 | 250 | 250 |
| cesium [ppmwt] | 150 | 550 | 750 |
| tungsten [ppmwt] | 400 | 120 | 200 |

Catalyst Test Method

A pressure-resistant steel reactor enclosed by a thermostatically controlled jacket was charged with the comparative catalysts 1 and 2 and the catalysts A and B of the invention in all cases without having been crushed in an amount of 13 dm$^3$ in each case. A gas having the following composition was passed through the reactor: 30 vol % of ethylene, 8 vol % of oxygen, 6.5 vol % of $CO_2$, 4 vol % of argon, 4 vol % of steam, 3 ppm of vinyl chloride, remainder methane. The pressure during the reaction was 16 bar. The temperature in the reactor was controlled via the heat regulating liquid such that at a space velocity of 3300 $m^3$(STP) of gas per $m^3$ of catalyst per hour an oxygen conversion of 35% was achieved. Samples were taken following a period of 4 d and the selectivity of the conversion of ethylene toward the formation of ethylene oxide and the activity (expressed in terms of the temperature required to attain a 35% oxygen conversion) were determined. The results obtained using this test method on the individual catalysts are listed in Table 3 below.

TABLE 3

| Catalyst | Comparative Catalyst 1 | Comparative Catalyst 2 | A | B |
| --- | --- | --- | --- | --- |
| Selectivity | 80.0 | 81.3 | 82.0 | 82.2 |
| Activity (°C.) | 228 | 251 | 226 | 221 |

We claim:
1. An improved catalyst in which silver is applied to an aluminum oxide support for the direct oxidation of ethylene with oxygen to form ethylene oxide which comprises:
a catalyst consisting essentially of silver together with at least one alkali metal as a first promoter and tungsten as a second promoter applied to a porous support substantially consisting of α-aluminum oxide having a specific surface area (BET) of from 0.3 to 3 $m^2$/g, the amount of said tungsten applied to the support being from 60 to 280 ppmwt, based on the total catalyst, per $m^2$ of surface area for each gram of said support.

2. An improved catalyst as claimed in claim 1, wherein the silver content, based on the total catalyst, is from 10 to 30% by weight.

3. An improved catalyst as claimed in claim 1, wherein the alkali metal is selected from the group consisting of lithium, rubidium, cesium and mixtures thereof.

4. An improved catalyst as claimed in claim 1, wherein the alkali metal is a mixture of lithium and cesium.

5. An improved catalyst as claimed in claim 1, wherein the content of rubidium, cesium or mixtures thereof is from 200 to 2000 ppmwt and the content of lithium is from 100 to 1000 ppmwt, based in each case on the total catalyst.

6. An improved catalyst as claimed in claim 1, wherein the purity of the α-aluminum oxide support is more than 99 wt %.

7. An improved catalyst as claimed in claim 1, wherein the purity of the α-aluminum oxide support is more than 99.5 wt %.

8. An improved catalyst as claimed in claim 7, wherein the α-aluminum oxide support has a specific surface area (BET) of from 0.5 to 2.0 $m^2$/g.

* * * * *